(12) United States Patent
Marnay et al.

(10) Patent No.: US 9,956,086 B2
(45) Date of Patent: *May 1, 2018

(54) INTERVERTEBRAL IMPLANT, INSERTION TOOL AND METHOD OF INSERTING SAME

(71) Applicant: CENTINEL SPINE LLC, New York, NY (US)

(72) Inventors: Thierry Marnay, Montpellier (FR);
Rudolf Bertagnoli, Straubing (DE);
Francis P. Magee, Mackay, ID (US);
Stephan Eckhof, Tuttingen (DE)

(73) Assignee: CENTINEL SPINE LLC, New York, NY (US)

(*) Notice: Subject to any disclaimer, the term of this patent is extended or adjusted under 35 U.S.C. 154(b) by 0 days. days.

This patent is subject to a terminal disclaimer.

(21) Appl. No.: 15/433,029

(22) Filed: Feb. 15, 2017

(65) Prior Publication Data

US 2017/0156886 A1 Jun. 8, 2017

Related U.S. Application Data

(63) Continuation of application No. 14/793,130, filed on Jul. 7, 2015, now Pat. No. 9,585,763, which is a
(Continued)

(51) Int. Cl.
*A61F 2/44* (2006.01)
*A61F 2/46* (2006.01)
*A61F 2/30* (2006.01)

(52) U.S. Cl.
CPC ........ *A61F 2/4425* (2013.01); *A61F 2/30771* (2013.01); *A61F 2/4611* (2013.01);
(Continued)

(58) Field of Classification Search
CPC .......... A61F 2002/444; A61F 2002/443; A61F 2/4425; A61F 2/44; A61F 2/442
See application file for complete search history.

(56) References Cited

U.S. PATENT DOCUMENTS

| 114,816 A | 5/1871 | Hiestand |
| 3,486,505 A | 12/1969 | Morrison |

(Continued)

FOREIGN PATENT DOCUMENTS

| DE | 2263842 A1 | 7/1974 |
| DE | 2804936 A1 | 8/1979 |

(Continued)

OTHER PUBLICATIONS

FR 2737656 A1, (2 pages), 1997.
(Continued)

*Primary Examiner* — Julianna N Harvey
(74) *Attorney, Agent, or Firm* — Farber LLC

(57) ABSTRACT

An intervertebral implant, alone and in combination with an insertion tool for inserting same and a method for inserting same. The implant has upper and lower parts which have universal movement relative to each other. Each of the upper and lower parts also has a surface engaging an adjacent vertebrae. Each part has a keel extending from said surface into a cutout in the adjacent vertebrae, and each keel has an anterior opening recess therein. An insert tool has a pair of arms which are received in the recess of the keels through the anterior opening to securely hold and insert the implant. Projections and matching indentations in each arm and the base of its recess securely attached each arm within its keel.

13 Claims, 8 Drawing Sheets

Related U.S. Application Data continuation of application No. 14/063,389, filed on Oct. 25, 2013, now Pat. No. 9,084,682, which is a continuation of application No. 13/347,461, filed on Jan. 10, 2012, now Pat. No. 8,579,978, which is a continuation of application No. 11/669,273, filed on Jan. 31, 2007, now Pat. No. 8,105,381, which is a continuation of application No. 10/318,078, filed on Dec. 13, 2002, now Pat. No. 7,204,852.

(52) U.S. Cl.
CPC . *A61F 2002/305* (2013.01); *A61F 2002/3092* (2013.01); *A61F 2002/3093* (2013.01); *A61F 2002/30383* (2013.01); *A61F 2002/30604* (2013.01); *A61F 2002/30616* (2013.01); *A61F 2002/30662* (2013.01); *A61F 2002/30827* (2013.01); *A61F 2002/30884* (2013.01); *A61F 2002/443* (2013.01); *A61F 2002/4628* (2013.01); *A61F 2220/0025* (2013.01); *A61F 2310/00017* (2013.01); *A61F 2310/00023* (2013.01); *A61F 2310/00029* (2013.01); *A61F 2310/00059* (2013.01); *A61F 2310/00101* (2013.01); *A61F 2310/00179* (2013.01); *A61F 2310/00407* (2013.01)

(56) References Cited

U.S. PATENT DOCUMENTS

| | | |
|---|---|---|
| 3,579,829 A | 5/1971 | Sampson |
| 3,875,595 A | 4/1975 | Froning |
| 4,021,864 A | 5/1977 | Waugh |
| 4,034,746 A | 7/1977 | Williams |
| 4,038,897 A | 8/1977 | Murray et al. |
| 4,038,987 A | 8/1977 | Komiya |
| 4,232,404 A | 11/1980 | Samuelson et al. |
| 4,309,777 A | 1/1982 | Patil |
| 4,349,921 A | 9/1982 | Kuntz |
| 4,467,802 A | 8/1984 | Maslanka |
| 4,545,374 A | 10/1985 | Jacobson |
| 4,697,586 A | 10/1987 | Gazale |
| 4,714,469 A | 12/1987 | Kenna |
| 4,736,738 A | 4/1988 | Lipovsek et al. |
| 4,759,766 A | 7/1988 | Buttner-Janz et al. |
| 4,863,476 A | 9/1989 | Shepperd |
| 4,898,161 A | 2/1990 | Grundei |
| 4,946,378 A | 8/1990 | Hirayama et al. |
| 4,997,432 A | 3/1991 | Keller |
| 5,122,130 A | 6/1992 | Keller |
| 5,171,280 A | 12/1992 | Baumgarnter |
| 5,211,645 A | 5/1993 | Baumgart et al. |
| 5,228,455 A | 7/1993 | Barcel |
| 5,236,460 A | 8/1993 | Barber et al. |
| 5,258,031 A | 11/1993 | Salib et al. |
| 5,306,308 A | 4/1994 | Gross et al. |
| 5,306,309 A | 4/1994 | Wagner et al. |
| 5,314,477 A | 5/1994 | Marnay |
| 5,336,232 A | 8/1994 | Green et al. |
| 5,364,397 A | 11/1994 | Hayes et al. |
| 5,370,697 A | 12/1994 | Baumgartner |
| 5,383,888 A | 1/1995 | Zvenyatsky et al. |
| 5,395,317 A | 3/1995 | Kambin |
| 5,401,269 A | 3/1995 | Buttner-Janz et al. |
| 5,409,492 A | 4/1995 | Jones et al. |
| 5,423,825 A | 6/1995 | Levine |
| 5,425,773 A | 6/1995 | Boyd et al. |
| 5,431,658 A | 7/1995 | Moskovich |
| 5,443,514 A | 8/1995 | Steffee |
| 5,484,437 A | 1/1996 | Michelson |
| 5,489,307 A | 2/1996 | Kuslich et al. |
| 5,501,654 A | 3/1996 | Failla et al. |
| 5,505,732 A | 4/1996 | Michelson |
| 5,507,816 A | 4/1996 | Bullivant |
| 5,554,191 A | 9/1996 | Lahille et al. |
| 5,556,431 A | 9/1996 | Buttner-Janz et al. |
| 5,562,736 A | 10/1996 | Ray et al. |
| 5,562,738 A | 10/1996 | Boyd et al. |
| 5,571,109 A | 11/1996 | Bertagnoli |
| 5,676,701 A * | 10/1997 | Yuan ............... A61L 27/045 606/247 |
| 5,702,469 A | 12/1997 | Whipple et al. |
| 5,716,415 A | 2/1998 | Steffee |
| 5,720,751 A | 2/1998 | Jackson |
| 5,722,977 A | 3/1998 | Wilhelmy |
| 5,776,199 A | 7/1998 | Michelson |
| 5,782,830 A | 7/1998 | Farris |
| 5,782,832 A | 7/1998 | Larsen et al. |
| 5,797,909 A | 8/1998 | Michelson |
| 5,824,094 A | 10/1998 | Serhan et al. |
| D401,335 S | 11/1998 | Koros et al. |
| 5,885,300 A | 3/1999 | Tokuhashi et al. |
| 5,888,226 A | 3/1999 | Rogozinski |
| 5,895,428 A | 4/1999 | Berry |
| 5,897,593 A | 4/1999 | Kohrs et al. |
| 5,899,901 A | 5/1999 | Middleton |
| 5,899,941 A | 5/1999 | Nishijima et al. |
| 5,951,564 A | 9/1999 | Schroder et al. |
| 6,006,174 A | 12/1999 | Lin et al. |
| 6,017,342 A | 1/2000 | Rinner |
| 6,019,792 A | 2/2000 | Cauthen |
| 6,033,405 A | 3/2000 | Winslow et al. |
| 6,036,692 A | 3/2000 | Burel et al. |
| 6,042,582 A | 3/2000 | Ray et al. |
| 6,059,790 A | 5/2000 | Sand et al. |
| 6,063,088 A | 5/2000 | Winslow |
| 6,080,155 A | 6/2000 | Michelson |
| 6,083,225 A | 7/2000 | Winslow et al. |
| 6,086,595 A | 7/2000 | Yonemura et al. |
| 6,096,038 A | 8/2000 | Michelson |
| 6,102,950 A | 8/2000 | Vaccaro |
| 6,110,179 A | 8/2000 | Flivik et al. |
| 6,113,602 A | 9/2000 | Sand |
| 6,113,637 A * | 9/2000 | Gill ............... A61F 2/4425 623/17.15 |
| 6,113,638 A | 9/2000 | Williams et al. |
| 6,117,174 A | 9/2000 | Nolan |
| 6,126,660 A | 10/2000 | Dietz |
| 6,126,674 A | 10/2000 | Janzen |
| 6,146,421 A | 11/2000 | Gordon et al. |
| 6,156,040 A | 12/2000 | Yonemura et al. |
| 6,156,067 A | 12/2000 | Bryan et al. |
| 6,159,215 A | 12/2000 | Urbahns et al. |
| 6,171,339 B1 | 1/2001 | Houfburg et al. |
| 6,174,311 B1 | 1/2001 | Branch et al. |
| 6,224,599 B1 | 5/2001 | Baynham et al. |
| 6,238,414 B1 | 5/2001 | Griffiths |
| 6,241,769 B1 | 6/2001 | Nicholson et al. |
| 6,261,296 B1 | 7/2001 | Aebi et al. |
| 6,270,498 B1 | 8/2001 | Michelson |
| 6,309,421 B1 | 10/2001 | Pisharodi |
| 6,368,350 B1 | 4/2002 | Erickson et al. |
| 6,368,351 B1 | 4/2002 | Glenn et al. |
| 6,402,785 B1 | 6/2002 | Zdeblick et al. |
| 6,436,139 B1 | 8/2002 | Shapiro et al. |
| 6,440,142 B1 | 8/2002 | Ralph et al. |
| 6,440,168 B1 | 8/2002 | Cauthern |
| 6,440,169 B1 | 8/2002 | Elberg et al. |
| 6,447,545 B1 | 9/2002 | Bagby |
| 6,447,547 B1 | 9/2002 | Michelson |
| 6,478,800 B1 | 11/2002 | Fraser et al. |
| 6,478,801 B1 | 11/2002 | Raphlh |
| 6,478,823 B1 | 11/2002 | Michelson |
| 6,500,206 B1 | 12/2002 | Bryan |
| 6,517,544 B1 | 2/2003 | Michelson |
| 6,558,424 B2 | 5/2003 | Thalgott |
| 6,565,574 B2 | 5/2003 | Michelson |
| 6,595,995 B2 | 7/2003 | Zdeblick et al. |
| 6,599,294 B2 | 7/2003 | Fuss et al. |
| 6,610,065 B1 | 8/2003 | Branch et al. |
| 6,613,091 B1 | 9/2003 | Zdeblick et al. |
| 6,635,060 B2 | 10/2003 | Hanson et al. |
| 6,641,582 B1 | 11/2003 | Hanson et al. |

(56) References Cited

U.S. PATENT DOCUMENTS

| | | |
|---|---|---|
| 6,652,533 B2 | 11/2003 | O'Neil |
| 6,652,534 B2 | 11/2003 | Zucherman et al. |
| 6,712,825 B2 | 3/2004 | Aebi et al. |
| 6,733,505 B2 | 5/2004 | Li |
| 6,746,454 B2 | 6/2004 | Winterbottom et al. |
| 6,755,841 B2 | 6/2004 | Fraser et al. |
| 6,770,074 B2 | 8/2004 | Michelson |
| 6,824,565 B2 | 11/2004 | Muhanna et al. |
| 6,875,213 B2 | 4/2005 | Michelson |
| 6,896,676 B2 | 5/2005 | Zubok et al. |
| 6,936,071 B1 | 8/2005 | Marnay et al. |
| 6,964,687 B1 | 11/2005 | Bernerd et al. |
| 6,966,912 B2 | 11/2005 | Michelson |
| 7,081,120 B2 | 7/2006 | Li et al. |
| 7,118,580 B1 | 10/2006 | Beyersdorff et al. |
| 7,169,182 B2 | 1/2007 | Errico et al. |
| 7,204,852 B2 | 4/2007 | Marnay et al. |
| 7,238,203 B2 | 7/2007 | Bagga et al. |
| 7,252,673 B2 | 8/2007 | Lim |
| 7,491,204 B2 | 2/2009 | Marnay |
| 7,547,309 B2 | 6/2009 | Bertagnoli et al. |
| 7,575,576 B2 | 8/2009 | Zubok et al. |
| 2002/0016633 A1 | 2/2002 | Lin et al. |
| 2002/0049497 A1 | 4/2002 | Mason |
| 2002/0072752 A1 | 6/2002 | Zucherman et al. |
| 2002/0077702 A1 | 6/2002 | Castro |
| 2002/0165612 A1 | 11/2002 | Gerber et al. |
| 2003/0069586 A1 | 4/2003 | Errico et al. |
| 2003/0083747 A1 | 5/2003 | Winterbottom et al. |
| 2003/0135275 A1 | 7/2003 | Garcia et al. |
| 2003/0208273 A1 | 11/2003 | Eisermann et al. |
| 2004/0030387 A1 | 2/2004 | Landry et al. |
| 2004/0143332 A1 | 7/2004 | Krueger et al. |
| 2004/0215198 A1 | 10/2004 | Marnay et al. |
| 2004/0225295 A1 | 11/2004 | Zubok et al. |
| 2005/0021042 A1 | 1/2005 | Marnay et al. |
| 2005/0143747 A1 | 6/2005 | Zubok et al. |
| 2005/0143749 A1 | 6/2005 | Zalenski et al. |
| 2005/0165408 A1 | 7/2005 | Puno et al. |
| 2005/0228500 A1 | 10/2005 | Kim et al. |
| 2005/0251260 A1 | 11/2005 | Gerber et al. |
| 2006/0030856 A1 | 2/2006 | Drewry et al. |
| 2006/0030860 A1 | 2/2006 | Peterson |
| 2006/0064100 A1 | 3/2006 | Bertagnoli et al. |
| 2006/0089656 A1 | 4/2006 | Allard et al. |
| 2006/0100633 A1 | 5/2006 | Michelson |
| 2006/0149273 A1 | 7/2006 | Ross et al. |
| 2006/0241641 A1 | 10/2006 | Albans et al. |
| 2007/0016221 A1 | 1/2007 | Beyersdorff et al. |
| 2007/0162134 A1 | 7/2007 | Marnay |

FOREIGN PATENT DOCUMENTS

| | | |
|---|---|---|
| DE | 3526742 | 1/1987 |
| DE | 4328690 | 3/1995 |
| DE | 29916078 | 11/1999 |
| EP | 0077159 | 4/1983 |
| EP | 0471821 | 2/1992 |
| EP | 0333990 | 7/1993 |
| EP | 0712607 | 5/1996 |
| EP | 1572041 | 9/2005 |
| FR | 2718635 | 10/1995 |
| FR | 2737656 | 2/1997 |
| FR | 2795945 | 1/2001 |
| JP | 2-261446 | 10/1990 |
| WO | WO 91/13598 | 9/1991 |
| WO | WO 98/34552 | 8/1998 |
| WO | WO 01/01893 | 1/2001 |
| WO | WO 01/12295 | 2/2001 |
| WO | WO 01/19295 | 3/2001 |
| WO | WO 02/071986 | 9/2002 |
| WO | WO 03/053290 | 7/2003 |

OTHER PUBLICATIONS

U.S. Appl. No. 10/070,823: Final Rejection dated Aug. 23, 2005, 11 pages.
U.S. Appl. No. 10/070,823: Non-Final Office Action dated Sep. 23, 2004, 10 pages.
U.S. Appl. No. 10/318,078: Final Rejection dated Aug. 1, 2006, 7 pages.
U.S. Appl. No. 10/318,078: Final Rejection dated Nov. 12, 2004, 7 pages.
U.S. Appl. No. 10/318,078: Issue Notification, dated Mar. 28, 2007, 1 page.
U.S. Appl. No. 10/318,078: Non-Final Office Action dated Apr. 21, 2004, 6 pages.
U.S. Appl. No. 10/318,078: Non-Final Office Action dated Aug. 8, 2005, 5 pages.
U.S. Appl. No. 10/318,078: Notice of Allowance dated Feb. 26, 2007, 6 pages.
U.S. Appl. No. 10/622,535: Final Rejection dated Feb. 6, 2009, 7 pages.
U.S. Appl. No. 10/622,535: Final Rejection dated May 23, 2006, 6 pages.
U.S. Appl. No. 10/622,535: Non-Final Office Action dated Jan. 31, 2008, 6 pages.
U.S. Appl. No. 10/622,535: Non-Final Office Action dated Apr. 26, 2007, 6 pages.
U.S. Appl. No. 10/622,535: Non-Final Office Action dated Nov. 8, 2006, 6 pages.
U.S. Appl. No. 10/622,535: Non-Final Office Action dated Aug. 30, 2005, 7 pages.
U.S. Appl. No. 10/622,535: Non-Final Office Action, dated Sep. 12, 2007, 6 pages.
U.S. Appl. No. 10/622,535: Notice of Allowance dated Jul. 20, 2009, 6 pages.
U.S. Appl. No. 10/622,535: Notice of Allowance, dated Nov. 17, 2009, 4 pages.
U.S. Appl. No. 11/512,327: Final rejection dated Jun. 23, 2009, 6 pages.
U.S. Appl. No. 11/512,327: Non-Final Office Action dated Oct. 6, 2008, 6 pages.
U.S. Appl. No. 11/512,327: Notice of Allowance dated Oct. 8, 2009, 4 pages.
U.S. Appl. No. 11/512,327: Notice of Allowance, dated Oct. 8, 2009, 4 pages.
U.S. Appl. No. 10/070,823: Notice of Allowance, dated Jul. 13, 2006, 4 pages.

* cited by examiner

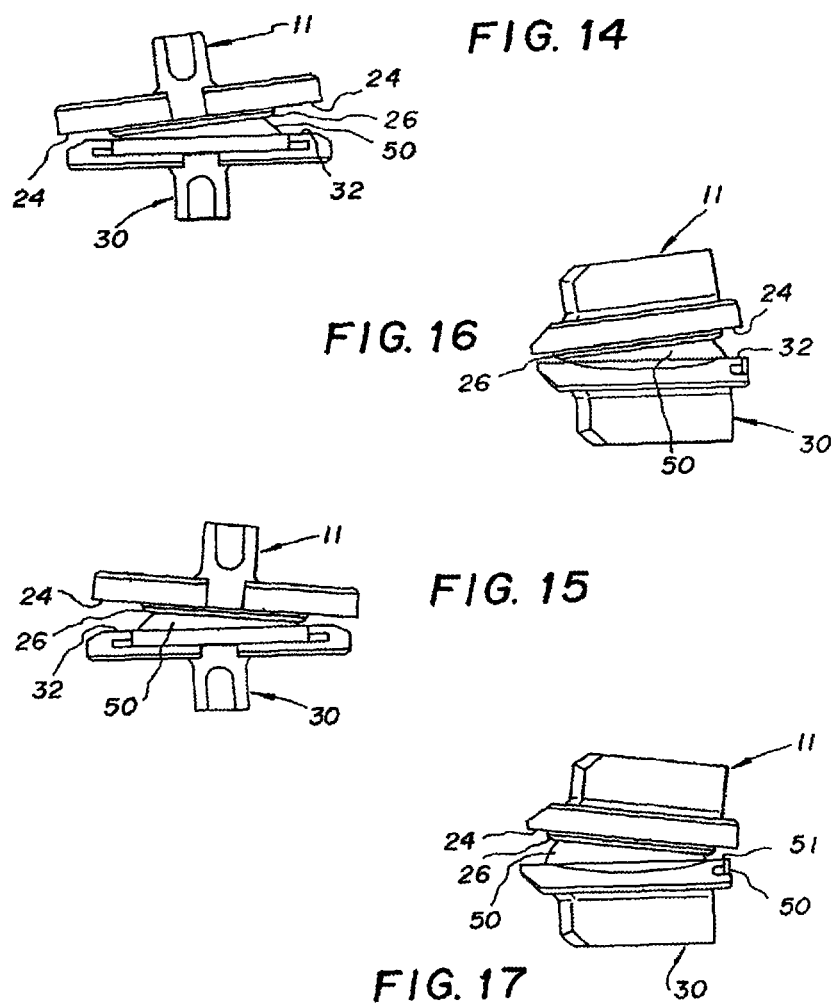

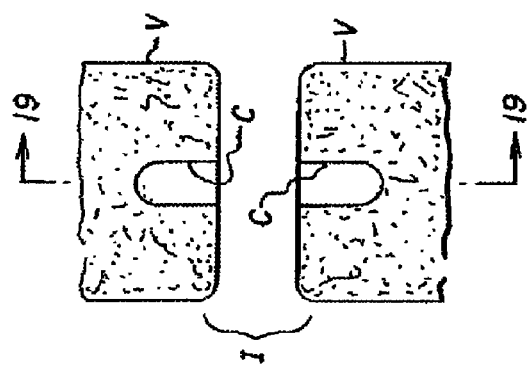
FIG. 18
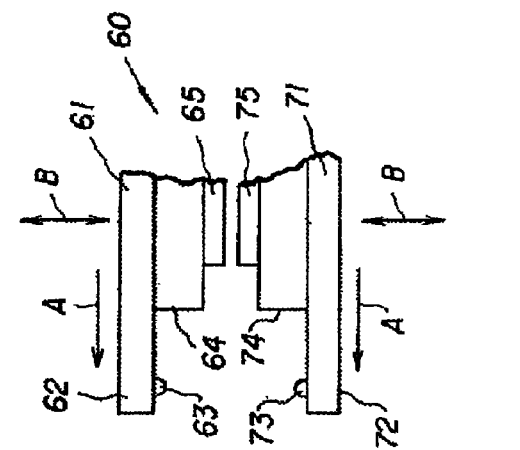
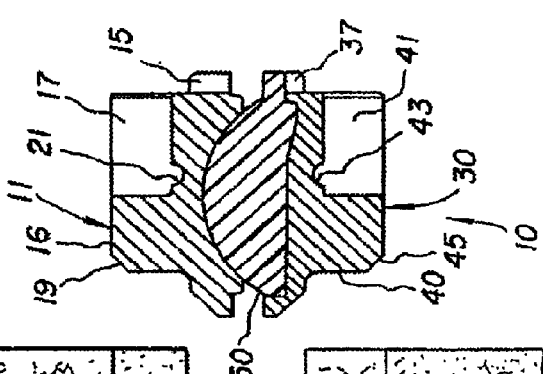
FIG. 19

INTERVERTEBRAL IMPLANT, INSERTION TOOL AND METHOD OF INSERTING SAME

CROSS REFERENCE TO RELATED APPLICATIONS

This application is a continuation of U.S. patent application Ser. No. 14/793,130 filed Jul. 7, 2015 which is a continuation U.S. patent application Ser. No. 14/063,389 filed Oct. 25, 2013, now U.S. Pat. No. 9,084,682 which is a continuation of U.S. patent application Ser. No. 13/347,461 filed Jan. 10, 2012, now U.S. Pat. No. 8,579,978 which is a continuation of U.S. patent application Ser. No. 11/669,273 filed Jan. 31, 2007, now U.S. Pat. No. 8,105,381 which is a continuation of U.S. patent application Ser. No. 10/318,078 filed Dec. 13, 2002, now U.S. Pat. No. 7,204,852 issue date Apr. 17, 2007; the disclosures of which are hereby incorporated by reference herein in their entireties.

FIELD OF THE INVENTION

This invention relates to intervertebral implants, and in particular, to a new and improved intervertebral implant and to an insertion tool and a method for inserting same.

BACKGROUND OF THE INVENTION

Historically, when it was necessary to completely remove a disc from between adjacent vertebrae, the normal remedy was to fuse the adjacent vertebrae together. More recently, there have been important developments in the field of disc replacement, namely disc arthroplasty which involves the insertion of an artificial intervertebral implant into the intervertebral space between adjacent vertebrae and which allows movement of the adjacent vertebrae relative to each other in flexion, extension, lateral bending, axial rotation and translation, as well as absorbing axial compression.

One such development is an artificial intervertebral implant as shown in Published Application No. WO 01/01893, published Jan. 11, 2001. The instruments for inserting same are shown in Published Application No. WO 01/19295, published Mar. 22, 2001.

While the intervertebral implant and instruments as shown in these publications represents a substantial improvement in the art, there exists a continuing need for improvements in the field of artificial intervertebral implants.

One such area in need of further improvements includes intervertebral implants for the intervertebral spaces between adjacent cervical vertebrae. This is because the cervical vertebrae and the dimensions of the intervertebral spaces between them are quite small. For example, the area of the cervical vertebral surfaces facing the adjacent cervical intervertebral spaces may be only about 20 percent of the intervertebral surfaces of the vertebrae in the lumbar region, thereby making this an extremely delicate area in which to insert an intervertebral implant.

BRIEF SUMMARY OF THE INVENTION

The purpose of the present invention is to provide a new and improved intervertebral implant, an insertion tool and a method for inserting same which are highly advantageous in the delicate and difficult area of the cervical spine. It is to be noted, however, that while the present invention has been developed particularly for the cervical spine, the invention is equally applicable for inserting an intervertebral implant at any location in the spine, including the lumbar spine.

Thus, although the invention has been developed and is particularly advantageous for the cervical spine, it will be described below more generally as an intervertebral implant without specifically identifying any particular portion of the spine.

It is thus an object of the present invention to provide a new and improved intervertebral implant together with an insertion tool and a method for inserting same.

It is another object of the present invention to provide an insertion tool and a method for inserting the new improved intervertebral implant.

In accordance with the present invention, there is provided an intervertebral implant having an upper part and a lower part which are operatively engaged for limited universal movement relative to each other. The upper part has a keel which is received in a cutout in the adjacent vertebrae, while the lower part has a keel which is received in a cutout in the other adjacent vertebrae. In accordance with a main feature of the present invention, these keels, in addition to providing an anchoring function within the adjacent vertebrae, include a recess open at an end thereof for receiving arms of an insertion tool. This has the advantage of allowing grasping the implant firmly but over a very limited area for inserting the implant into the intervertebral space with minimal invasion of the work area by the insertion tool.

The upper part preferably has a spherical concave portion formed in its lower surface. The lower part preferably has a plastic inlay attached thereto, which inlay has a raised spherical convex portion which engages the spherical concave portion of the upper part to provide the limited universal movement between the two.

The insertion tool usable in combination with the implant preferably has a pair of arms, each of which engages a recess within a keel, each arm having a projection which is moved toward the base of the recess to engage indentations in the base of the recesses to firmly hold the implant. The arms also include lateral support portions which engage support cutouts on the upper and lower parts to absorb lateral forces exerted on the implant so that such lateral forces do not have to be absorbed by the more delicate portions of the insertion tool arms located within the recesses of the keels.

The method of present invention comprises engaging an intervertebral implant of the type described with an insertion tool of the type described, inserting the intervertebral implant into the intervertebral space with the keels entering cutouts in the adjacent vertebrae, and then removing the insertion tool from the intervertebral implant, leaving the intervertebral implant in place within the intervertebral space.

Thus, it is an object of the present invention to provide a new and improved intervertebral implant.

It is another object of the present invention to provide an insertion tool and a method for inserting the new improved intervertebral implant.

It is another object of the present invention to provide an intervertebral implant which is particularly suitable for the cervical spine.

It is another object of the present invention to provide a new and improved intervertebral implant characterized by a recess in raised keels for receiving insertion tools for inserting the intervertebral implant.

These and other objects of the present invention will be apparent from the detailed description to follow, together with the accompanying drawings.

BRIEF DESCRIPTION OF THE DRAWINGS

A preferred embodiment of the invention will now be described by way of example with reference to the accompanying drawings, wherein:

FIGS. 14-17 are elevational views of the implant of FIG. 1 illustrating the limited universal movement of the parts thereof;

FIG. 18 is a schematic view of a pair of adjacent vertebrae prepared to receive an implant of the present invention in the intervertebral space therebetween;

FIG. 19 illustrates the vertebrae of FIG. 18, in a direction along line 19-19 of FIG. 18 and showing the implant itself about to be inserted and showing an insertion tool prior to engaging the implant;

DETAILED DESCRIPTION OF PREFERRED EMBODIMENTS

Figure 1:
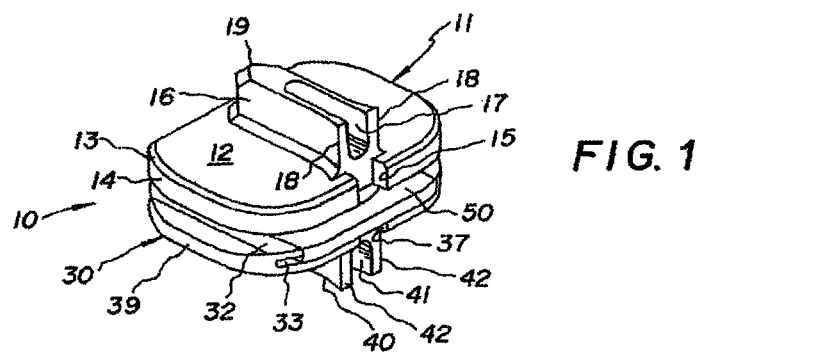
FIG. 1 is a perspective view of an intervertebral implant in accordance with the present invention.

Referring now to the figures, like elements are represented by like numerals throughout the several views.

In this application, the words "upper" or "lower" or "uppermost" or "lowermost" or any other words describing the orientation of the intervertebral implant of the present invention are used only for convenience and are not intended to convey any limitation. More specifically, the part of the implant described in this application as the upper part can in fact be positioned as the superior or inferior part within the patient's vertebrae with the other of the two parts being the opposite part. Also, since the intervertebral implant is normally inserted from the front of the patient, the side of the vertebrae toward which the intervertebral implant moves as it is inserted shall be referred to as the anterior side of the vertebrae and the opposite side as the posterior side and the right and left sides as lateral sides. Since the more common manner of insertion is anteriorly, the present invention will be described with respect to that orientation. Also, the posterior end of the implant may be referred to as the first end and the anterior end of the implant may be referred to as the second end. However, it is to be understood that the intervertebral implant can also be inserted laterally, i.e., from the side, in which case the keels will be oriented on the implant for such lateral movement and the cutouts in the adjacent vertebrae will be open toward a lateral side to receive the keel.

FIGS. 1-5 illustrate in different views the assembled intervertebral implant 10 including an upper part, or component, 11, a lower part, or component, 30 and a plastic inlay, or insert, 50 located therebetween but connected to the lower part 30.

The intervertebral implant of the present invention has been designed primarily for insertion in the cervical spine. This portion of the spine is characterized by the need for precision because of the relatively small dimensions of the cervical intervertebral space. For example, the implant of the present invention, when viewed in plan view (as best seen for example in FIG. 6) would be approximately 12-16 millimeters in width and approximately 15-19 millimeters in length. It has been found practical to provide three sizes, 12 millimeters×15 millimeters, 14 millimeters×17 millimeters and 16 millimeters×19 millimeters. The height of the implant, meaning the height from the upper surface of the upper part to the lower surface of the lower part, excluding the keels, would normally be between 5 millimeters and 9 millimeters. These dimensions are in contrast to an intervertebral disc to be located in the lumbar area wherein the rectangular portion would have dimensions more on the order of 27 to 30 millimeters in width, 34 to 39 millimeters in length, and a height of about 10 to 14 millimeters. However, it is to be understood that the features of the present invention are equally adaptable for an intervertebral implant of a different size and design for construction in any other part of the spine including the lumbar spine.

Figure 4:
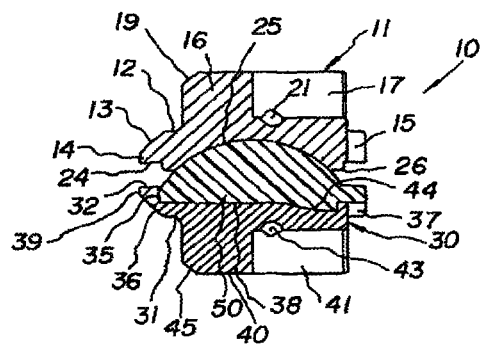
FIG. 4 is a cross sectional view taken along line 4-4 of FIG. 2.
Figure 5:
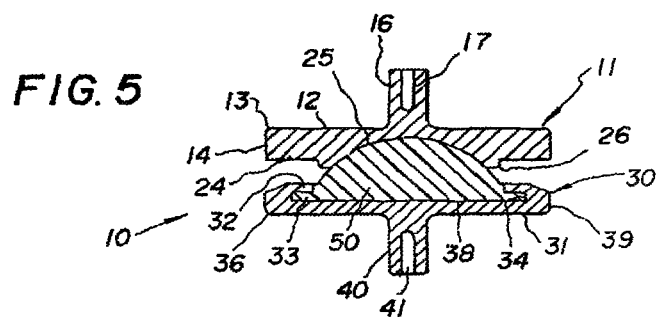
FIG. 5 is a cross sectional view taken along line 5-5 of FIG. 3.
Figure 6:
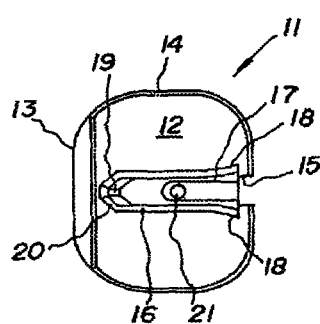
FIG. 6 is a top plan view of the upper part of the implant of FIG. 1.

The upper part 11 will now be described in detail with respect to FIGS. 1-5 which illustrate the assembled implant and FIGS. 6 and 7 which illustrate only the upper part 11. The upper part 11 includes an upper surface, or outer side, 12 which engages and supports the adjacent vertebral surface. This upper surface 12 is bounded by edges which are slightly beveled all the way around as shown at 13 with the largest portion of this bevel being along the posterior surface. Below the beveled edge 13, the upper part is bounded by a surrounding side wall 14 which has an anterior support cutout 15. Thus, in the figures the keels are shown oriented anterior to posterior with the solid portion of the keels facing posteriorly and the insertion engaging recess structure facing anteriorly.

Rising above the upper surface 12 of the upper part 11 is a keel 16 which includes a recess 17 formed therein. This recess is opened upwardly and anteriorly. Referring to FIGS. 4 and 6, this recess includes an indentation 21 in the base thereof. The posterior end of the keel 16 comprises a V-shaped upper bevel 19 and a V-shaped vertical portion 20, providing a front which is "arrow" shaped, as best seen in FIG. 6. The purpose of this "arrow" shape is to facilitate insertion of the keel into a cutout formed in the adjacent vertebrae. The anterior opening of the recess is flared at 18, which flare serves to anchor the anterior end of the keel 16 in its cutout in the adjacent vertebrae.

Figure 7:
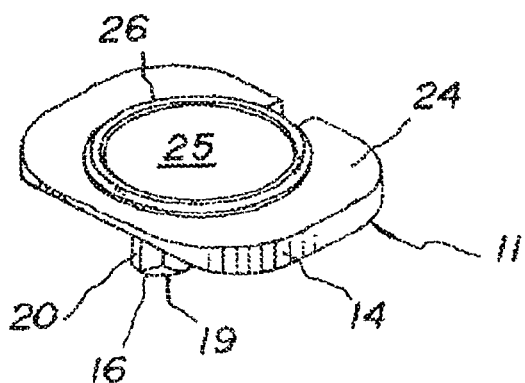
FIG. 7 is a perspective view of the bottom surface of the upper part of the implant of FIG. 1.

The upper part 11 includes a lower plane inner surface 24 which includes, as best seen in FIG. 7, a raised rim 26 which defines a rounded surface such as a concave spherical portion 25, which surface, along with a mating surface, provide for universal movement relative to each other. As best shown in FIGS. 4 and 5, this spherical concave portion 25 will mate with an upper convex surface of the plastic inlay 50.

Figure 8:
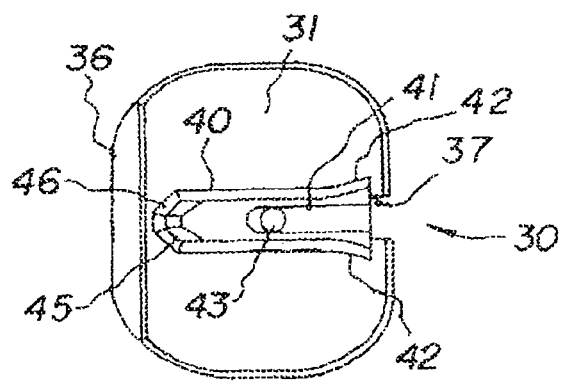
FIG. 8 is a bottom plan view of the lower part of the implant of FIG. 1.
Figure 9:
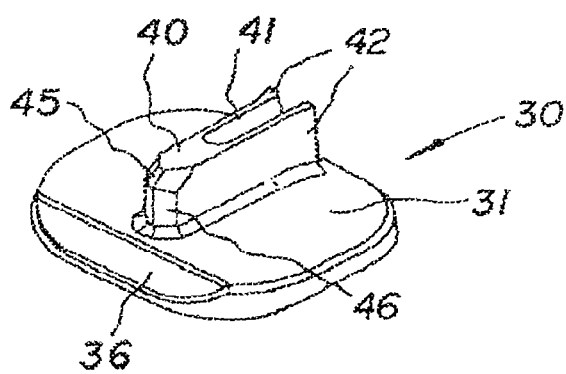
FIG. 9 is a bottom perspective view of the lower part of the implant of FIG. 1.
Figure 10:
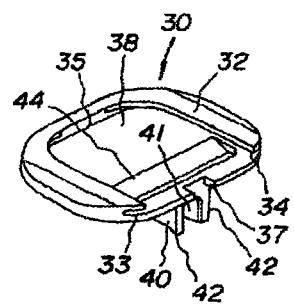
FIG. 10 is a top perspective view of the lower part of the implant of FIG. 1.

The lower part 30 is described with reference to FIGS. 1-5 and also FIGS. 8-10 which show isolated views of the lower part 30.

Figure 2:
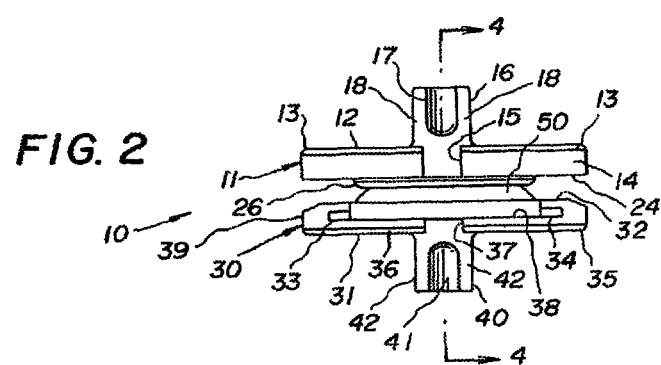
FIG. 2 is a front elevational view of the implant of FIG. 1.
Figure 3:
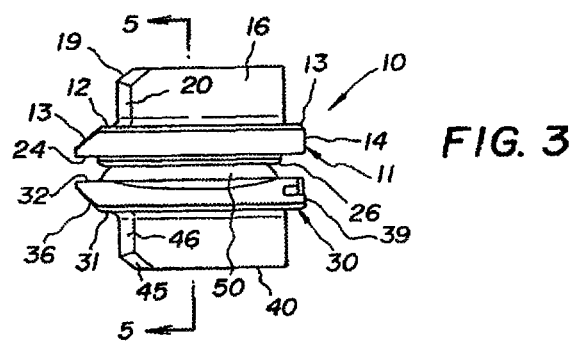
FIG. 3 is a left side elevational view of the implant of FIG. 1.
Figure 11:
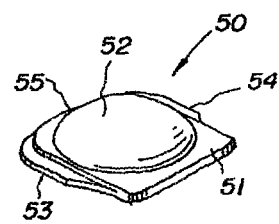
FIG. 11 is a top perspective view of the plastic inlay of the implant of FIG. 1.

The lower part 30 includes a lower vertebrae supporting and engaging surface, or outer side, 31 and an inner upper surface 32. As best seen in FIGS. 2, 5 and 10, this lower part includes grooves 33 and 34 formed in the interior side wall thereof beneath surface 32 and above a base surface 38. A substantially flat back wall 35 extends from base surface 38 to upper surface 32. This lower part includes a beveled edge 36 extending around the periphery of the lower surface 31 with a most pronounced bevel at the posterior thereof and a surrounding side wall 39. The purpose of the grooves 33 and 34 is to receive side flanges 53 and 54 of a plastic inlay 50, as shown in FIG. 11 and as will be described in greater detail below.

Lower part 30 includes an anterior support cutout 37. A keel 40 rises upwardly (or in the usual orientation, extends downwardly) from the lower surface 31. This keel includes a recess 41 which opens downwardly and anteriorly and has a flared anterior entrance to the recess at 42, which flared entrance serves the same function as flared entrance 18 of upper part 11, i.e., to facilitate engagement of the anterior end of the keel within its cutout in the vertebrae. As best shown in FIG. 4, the recess 41 opens downwardly and anteriorly and includes an indentation 43. The keel 40 includes at its posterior end a V-shaped lower bevel 45 and a V-shaped vertical portion 46 which together provide an "arrow" shape, as best seen in FIG. 8 to facilitate insertion of the keel into its cutout formed in the adjacent vertebrae. As seen in the figures, the recesses run along an anterior-posterior line of the implant.

Figure 13:
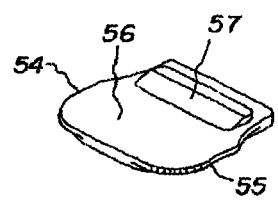
FIG. 13 is a bottom perspective view of the plastic inlay of the implant of FIG. 1.

Referring momentarily to FIG. 13, it will be noted that the lower surface of the plastic inlay 50 includes a raised snap-in projection 57. Referring now to FIG. 10, there is illustrated a snap-in recess 44 which is adapted to receive the snap-in projection 57 such that the plastic inlay can snap into place but is thereafter prevented from being removed. This snap fit is also shown clearly in FIG. 4. It will be noted, however, that while removal would not occur under normal circumstances, in fact it is possible at a subsequent time, by inserting a tool between the base of the lower part and the plastic inlay to pry the plastic inlay out and remove it. This might be useful, for example, if it were decided to insert a new plastic inlay of a different size or if it became necessary to repair the previously inserted plastic inlay.

The upper and lower parts are made of a suitable material such as titanium, cobalt chromium molybdenum, stainless steel or ceramics. The upper surface of the upper part and the lower surface of the lower part as well as the side surfaces of the keels are coated with a porous coating of titanium. The porosity of the coating ideally permits vascularization and osteoplast formation with subsequent bony on-growth.

Figure 12:
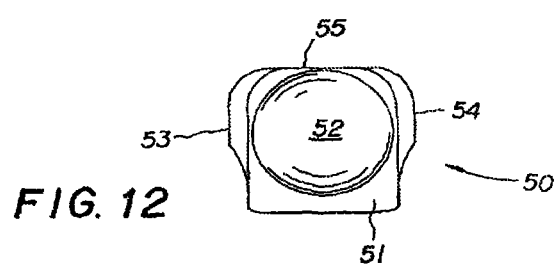
FIG. 12 is a top plan view of the plastic inlay of the implant of FIG. 1.
Figure 20:
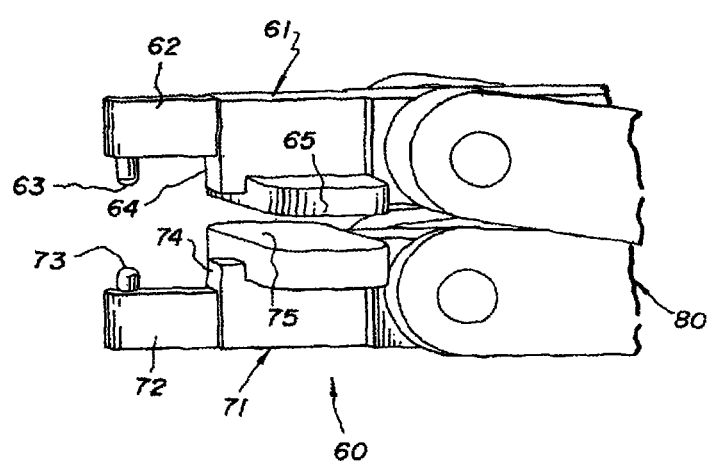
FIG. 20 illustrates a portion of an insertion tool for use with the implant of the present invention.

The plastic inlay 50 is visible in FIGS. 1-5. However, for convenience the numerals pointing to details thereof are not included in any of those figures, but instead are provided in FIGS. 11-13. It is preferably made of high density polyethylene. FIG. 11 illustrates the plastic inlay 50 in its position as shown in FIG. 1. It includes a flat upper surface 51 having attached thereto a rounded surface such as a convex spherical portion 52, which surface mates with the concave spherical portion 25 of the upper part 11 to provide for universal movement. Side flanges 53 and 54 engage the grooves 33 and 34 in the lower part 30. A flat posterior wall 55 engages the posterior wall 35 of the lower part.

Referring to FIG. 13, the plastic inlay 50 includes a generally flat lower surface 56 which engages the base surface 38 of the lower part and a snap-in projection 57 which is beveled on the posterior side and includes a sharp ledge on the anterior side so as to snap into place in the recess 44 of base surface 38 to the position as best shown in FIG. 4.

FIGS. 14-17 illustrate the limited universal movement of the upper and lower parts of the implant relative to each other when inserted in a patient's intervertebral space. FIGS. 14 and 15, both of which view the anterior of the implant, show maximum lateral bending to the left and right, respectively. It will be noted that in each case the raised rim 26 of the upper part 11 engages the inner surface 32 of the lower part 30. In a preferred embodiment, such lateral bending movement is possible for up to approximately 10.5° for the smaller of the three sizes and approximately 8.9° for the two larger sizes, relative to a reference position wherein the keels are aligned vertically. FIG. 16, which shows a view from the right side of the patient, shows extension movement of the upper part relative to the lower part which is limited by engagement of the rim 26 with the inner surface 32 of the lower part 30. Finally, FIG. 17, which is a view from the patient's left side, shows maximum flexion of the upper part 11 relative to the lower part 30. Flexion is limited by engagement of the rim 26 with the surface 51 of the inlay 50. In preferred embodiments, extension and flexion can occur up to approximately 10.5° for the smaller three sizes and approximately 8.9° for the two larger sizes, relative to a reference position wherein the keels are vertically aligned. As is apparent from the preceding discussion, the term "limited" as applied to universal movement refers to the limited range in each direction, as described above. However, as is also apparent, within that range, the movement is conventional universal movement in the sense that movement is allowed in all directions.

FIGS. 18-22 illustrate the method of insertion of the implant shown in FIGS. 1-17 and a portion of a handling instrument such as an insertion tool for use for inserting the implant.

FIG. 18 is an anterior view of a pair of adjacent vertebrae V on opposite sides of a cleaned-out intervertebral space I. In preparation for inserting the intervertebral implant of the present invention, cutouts C will be formed in the vertebrae V. As shown in FIG. 18 and the left hand portion of FIG. 19, these cutouts start from the anterior of the vertebrae and extend for most but not all of the distance toward the posterior of the vertebrae, intersecting along its entire length with the surface of the vertebrae facing into the intervertebral space.

FIG. 19 illustrates just to the right of the prepared adjacent vertebrae the intervertebral implant assembled in the form as shown in FIGS. 1-5. To the right thereof is an insertion tool 60 which is to be described with respect to FIGS. 19 and 20. This insertion tool 60 includes an upper arm 61 and a lower arm 71, which arms are arranged to move towards and away from each other as indicated by the arrows B in FIG. 19. Various devices can be provided for moving these arms towards and away from each other. One such mechanism in the form of a scissors is partially shown at 80 in FIG. 20. The upper and lower arms include keel engaging portions 62 and 72 which engage recesses 17 and 41, respectively. These arms include towards their outer ends projections 63 and 73 which are constructed to be received in the indentations 21 and 43, respectively. It will be noted that these keel engaging portions 62 and 72 are relatively narrow. In fact, it is contemplated that the entire width of each keel will be approximately 2 millimeters, thus allowing less than 2 millimeters for the actual recesses. The arms 61 and 71 also include lateral support surfaces 64 and 74 which, upon engagement of the tool with the implant, will engage the front support cutouts 15 and 37.

The arms 61 and 71 will be spaced apart from each other just enough for the projections 63 and 73 to clear the bottoms of the recesses 17 and 41 until the projections 63 and 73 reach the indentations 21 and 43, at which time the arms 61 and 71 will be moved towards each other such that the projections 63 and 73 engage within the indentations 21 and 43 and the lateral support surfaces 64 and 74 are engaged within the cutouts 15 and 37. At this position, abutment surfaces 65 and 75 on the upper arm and lower arm 61 and 71, respectively, will abut each other, thus limiting further movement of the arms 61 and 71 towards each other.

Figure 21:
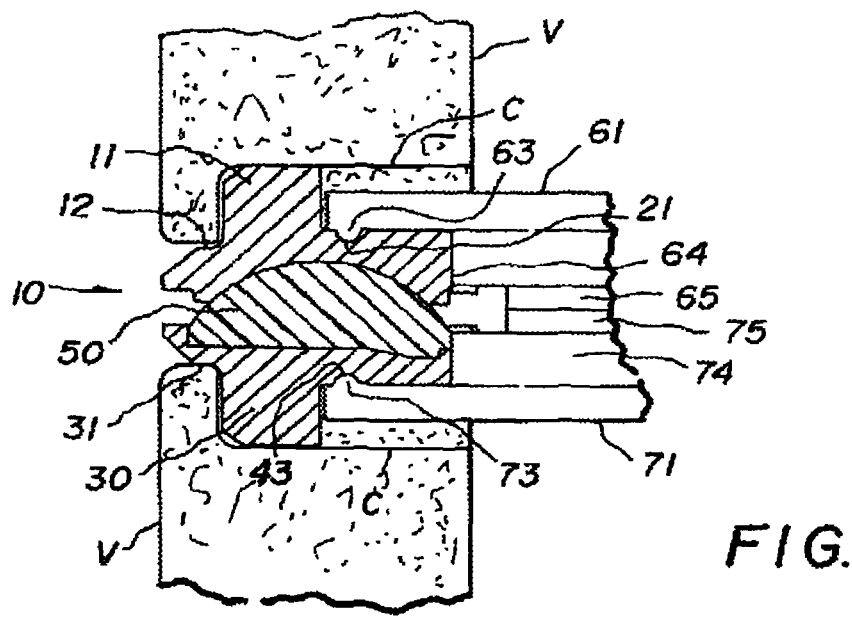
FIG. 21 illustrates the vertebrae of FIG. 18 with the implant in place therein and the insertion tool still holding the implant in the same position in which it held the implant during insertion.

With the assembled implant thus attached to the insertion tool, the insertion tool moves it into the intervertebral space with the keels 16 and 40 entering the cutouts C, while the portions of the upper and lower parts 11 and 30 posterior of the keels extends within the intervertebral space beyond the cutouts C so that upper surface 12 engages the intervertebral surface of the adjacent vertebrae V posterior of and adjacent to the keel 16 and surface 31 of the lower part 30 engages the intervertebral surface of the adjacent lower vertebrae posterior and adjacent to the keel 40. Actually, the above described engagement of the insertion tool 60 and the implant 10 prior to insertion is the same as shown in FIG. 21, just after insertion.

Figure 22:
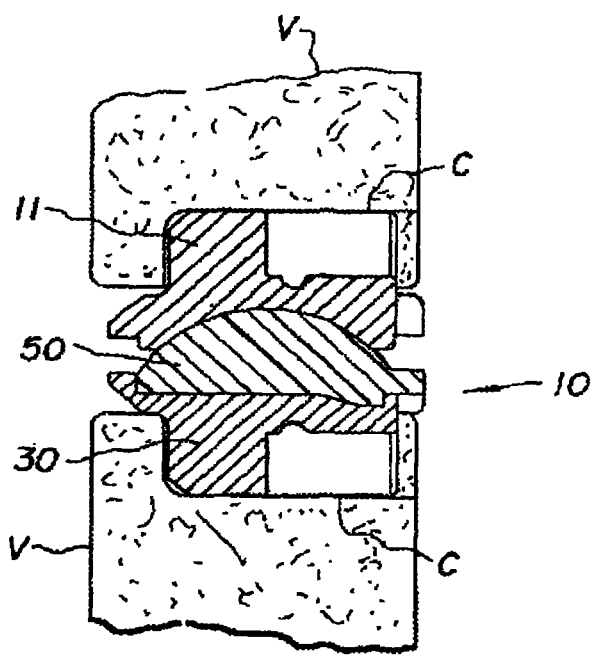
FIG. 22 illustrates the vertebrae with the implant in place and the insertion tool removed.

It will be noted that in FIG. 21 there is a space above and below the arms 61 and 71 within keel recesses 17 and 41, the vertical dimension of which spaces is greater than the height of the projection 63 and 73, which would normally be about 1.2 millimeters. This is necessary so that the arms 61 and 71 can be moved upwardly and downwardly, respectively, away from the base of their respective recesses to free the projections from the indentations before the upper and lower surfaces of arms 61 and 71 engage the vertebrae at the vertical extremities of the cutouts C. Such contact is to be avoided. Once these arms have been separated accordingly, they can be moved out from the implant, anteriorly, leaving the implant in place as shown in FIG. 22.

The method of the present invention will be apparent from the above described operation of the invention as shown and described with respect to FIGS. 18-22. In accordance with this method of the present invention, adjacent vertebrae are provided with cutouts in the manner described and an intervertebral implant of the type described is grasped with an insertion tool having arms which are received in the recesses of the keels through the anterior openings thereof. With the implant firmly grasped by the insertion tool, the implant is inserted anteriorly with the keels leading the way into the cutouts until the proper position has been reached. At this time, naturally some force will have been exerted to distend the adjacent vertebrae from each other, but preferably just enough to allow the implant to be inserted. In fact, many professionals prefer to distend the adjacent vertebrae no more than essentially the width between the upper and lower surfaces 12 and 31 and then apply additional external force with a mallet or the like to complete insertion of the implant. After the implant has been inserted, the arms of the insertion tool are separated just enough to free the projection/indentation engagements from each other, whereupon the insertion tool is removed anteriorly, leaving the implant in place and relieving any previously applied forces applied to distend the adjacent vertebrae from each other, allowing these adjacent vertebrae to rest upon the supporting surfaces 12 and 31 of the implant.

Although the invention has been described in detail with respect to preferred embodiments thereof, it will be apparent to one skilled in the art that the invention is capable of numerous modifications and variations within the spirit and scope of the invention.

What is claimed:

1. In combination, an intervertebral implant and a handling instrument, the combination comprising:
   the implant including:
      an upper part having an upper surface that is configured and adapted to engage a first vertebra that is spaced from a second vertebra so as to define an intervertebral space therebetween; and
      a lower part pivotally coupled to the upper part such that the upper and lower parts are pivotally movable relative to each other, the lower part having a lower surface that is configured and adapted to engage the second vertebra, wherein each of the upper part and lower part defines a trailing end and a leading end that is spaced from the trailing end along an insertion direction into the intervertebral space;
   the upper part including an upper keel extending along the insertion direction and that includes first and second side walls that each extend out from the upper surface such that when the implant is inserted into the intervertebral space, the upper keel is positioned at least partially within a cutout formed in the upper vertebra, the upper keel having a length along the insertion direction and a width along a lateral direction, the lateral direction being perpendicular to the insertion direction and substantially parallel to the upper surface, the length of the upper keel being greater than the width of the upper keel; and
   the lower part including a lower keel extending along the insertion direction and that includes first and second side walls that each extend out from the lower surface such that when the implant is inserted into the intervertebral space, the lower keel is positioned at least partially within a cutout formed in the lower vertebra;
   wherein the implant includes an upper recess partially defined by the side walls of the upper keel, and a lower recess partially defined by the side walls of the lower keel, and the upper and lower recesses extend into their respective keels along the insertion direction; and
   the handling instrument including:
      an upper arm and a lower arm that are configured to be inserted into the upper and lower recesses, respectively, along the insertion direction such that the handling instrument holds the implant during insertion of the implant into the intervertebral space.

2. The combination as recited in claim 1, wherein the implant further comprises an insert disposed between the upper part and the lower part, the insert connecting the upper part and the lower part so as to permit relative movement between the upper part and the lower part.

3. The combination as recited in claim 2, wherein the insert includes a rounded surface, and the insert rounded surface mates with a rounded surface of one of the upper part or the lower part to provide the relative movement between the upper part and the lower part.

4. The combination as recited in claim 3, wherein the mated rounded surfaces provide limited universal movement between the upper part and the lower part.

5. The combination as recited in claim 1, wherein the upper part and the lower part move relative to each other along a rounded mating surface.

6. The combination as recited in claim 5, wherein the rounded mating surface provides limited universal movement between the upper part and the lower part.

7. The combination as recited in claim 1, wherein the upper recess and the upper arm have corresponding shapes, and wherein the lower recess and the lower arm have corresponding shapes.

8. The combination as recited in claim 1, wherein the upper and lower recesses are configured to receive the handling instrument such that the handling instrument does not contact the first vertebra or the second vertebra during insertion of the implant into the intervertebral space.

9. The combination as recited in claim 1, wherein the handling instrument is an insertion tool.

10. The combination as recited in claim 1, wherein the upper keel and the lower keel each define a trailing end and a leading end spaced from the trailing end along the insertion direction, the leading end of the upper keel is offset from the leading end of the upper part in a direction opposite the insertion direction, and the leading end of the lower keel is offset from the leading end of the lower part in the direction opposite the insertion direction.

11. The combination as recited in claim 10, wherein the trailing end of the upper keel is offset from the trailing end of the upper part in the insertion direction, and the trailing end of the lower keel is offset from the trailing end of the lower part in the insertion direction.

12. The combination as recited in claim 1, wherein the upper keel and the lower keel each define a trailing end and a leading end spaced from the trailing end along the insertion direction, the trailing end of the upper keel is offset from the trailing end of the upper part in the insertion direction, and the trailing end of the lower keel is offset from the trailing end of the lower part in the insertion direction.

13. The combination as recited in claim 1, wherein the lower keel has a length along the insertion direction and a width along the lateral direction, the length of the lower keel being greater than the width of the lower keel.

* * * * *